United States Patent [19]

Quittmann et al.

[11] Patent Number: 5,187,297
[45] Date of Patent: Feb. 16, 1993

[54] PROCESS FOR THE PRODUCTION OF 3-AMINOCROTONONITRILE

[75] Inventors: Wilhelm Quittmann, Visp; Leo Zumoberhaus, Burchen; Peter Ruppen, Visp, all of Switzerland

[73] Assignee: Lonza Ltd., Gampel/Valais, Switzerland

[21] Appl. No.: 786,778

[22] Filed: Nov. 1, 1991

[30] Foreign Application Priority Data

Nov. 5, 1990 [CH] Switzerland ............... 3504/90

[51] Int. Cl.$^5$ .................. C07C 253/00; C07C 253/30
[52] U.S. Cl. ........................................ 558/360
[58] Field of Search ........................ 558/360

[56] References Cited

U.S. PATENT DOCUMENTS

| | | | |
|---|---|---|---|
| 3,290,355 | 12/1966 | Kunisch et al. | 558/360 |
| 3,973,025 | 8/1976 | Ward | 424/263 |
| 4,510,099 | 4/1985 | Stern | 558/360 |
| 5,089,651 | 2/1992 | Taniguchi et al. | 558/360 |

FOREIGN PATENT DOCUMENTS

| | | | |
|---|---|---|---|
| 3231052A1 | 2/1984 | Fed. Rep. of Germany | 558/360 |
| 415603 | 6/1966 | Switzerland . | |
| 1434654 | 5/1976 | Switzerland . | |
| 993300 | 5/1965 | United Kingdom | 558/360 |

OTHER PUBLICATIONS

Chemical Abstracts, vol. 85, 177262 (1976), Ward.
Chemical Abstracts, vol. 79, 53185b (1973), Boehner.
Chemical Abstracts, vol. 80 122383 (1974), Groebke, et al.
Takeda, et al., J. Pharm. Chem. Soc., Japan, 75, (1955), pp. 957 to 959.
Ziegler et al., Justus Liebigs Annalen, 504, (1933), p.115.
Krueger, J. Organometal. Chem. 9, (1967), pp. 125 to 134.
F. W. Bergstroem and W. C. Frenelius, Chem. Rev., 12 (1933), pp. 43 to 49, 134, 135 and 166 to 173 and 176 to 179.

*Primary Examiner*—Joseph Paul Brust
*Attorney, Agent, or Firm*—Fisher, Christen & Sabol

[57] ABSTRACT

A process for the production of 3-aminocrotononitrile by dimerization of acetonitrile. In this process, the deprotonation step takes place with sodium amide as a strong base in the presence of liquid ammonia. 3-Aminocrotononitrile is used as an initial product for the production of pharmaceutical agents, pesticides or azo dyes.

16 Claims, No Drawings

PROCESS FOR THE PRODUCTION OF 3-AMINOCROTONONITRILE

BACKGROUND OF THE INVENTION

1. Field Of The Invention

The invention comprises a new process for the production of 3-aminocrotononitrile by the dimerization of acetonitrile.

2. Background Art

3-Aminocrotononitrile is an intermediate product with a very wide spectrum of use. Thus, it is used, e.g., for the production of pharmaceutical agents (Chemical Abstracts, 85, 177262), the production of pesticides (Chemical Abstracts, 79, 53185b) and the production of azo dyes (Chemical Abstracts, 80, 122383).

Numerous processes are known for producing 3-aminocrotononitrile by the dimerization of acetonitrile in the presence of strong bases. But it is problematic in this reaction that acetonitrile with a base, such as, an amide ion, can react in various ways. Namely, if the nitrile group is attacked, the undesirable acetamidine is formed with the amide ion. Only the deprotonation of the acetonitrile to carbanion forms the prerequisite for the production of the desired 3-aminocrotononitrile.

Thus, according to Takeda et al., J. Pharm. Chem. Soc., Japan, 75, (1955), pages 957 to 959, a mixture of 3-aminocrotononitrile and acetamidine resulted after the reaction of acetonitrile with sodium amide at 100° C. for 3 hours.

Subsequently, an attempt was made to foster the carbanion formation by specific performance of the reaction, i.e., by the use of sterically-demanding, strong bases.

Building upon the studies of Ziegler et al., Justus Liebigs Annalen, 504, (1933), 115, in which acetonitrile with lithium diethylamide as a base was reacted specifically to 3-aminocrotononitrile (iminonitrile) with 86 percent yield, Krueger, J. Organonmetal. Chem., 9, (1967), pages 125 to 134, synthesized 3-aminocrotononitrile with sodium-bistrimethylsilylamide in 90 percent yield. Except for the very good yields, the above-mentioned syntheses have the drawback that the sterically-demanding bases had to be produced—in part—in a complicated and particularly expensive manner, which constitutes an obstacle to the application of these processes in large-scale operations for economic reasons. (Separate comparison examples below make this clear.)

But it is also known from Swiss Patent No. 415,603 (and U.S. Pat. No. 3,290,355) to condense acetonitrile to 3-aminocrotononitrile with the help of sodium in an aliphatic hydrocarbon as the solvent at 70° to 180° C. in a yield of 90 percent. This dimerization has the drawback that, because of the reaction mechanism, 3 moles of acetonitrile relative to 2 moles of sodium have to be used instead of 2 moles of acetonitrile relative to 1 mol of sodium or a base. Even though this process constitutes an operating method, it is uneconomical for such reasons and is also unecological because of the accumulation of sodium cyanide.

BROAD DESCRIPTION OF THE INVENTION

The main object of the invention is to provide a process which eliminates the above-mentioned drawbacks and by which 3-aminocrotononitrile can be produced ecologically and economically on a large scale. Other objects and advantages of the invention are set out herein or are obvious herefrom to one skilled in the art.

The objects and advantages of the invention are achieved by the invention process.

The invention involves a process for the production of 3-aminocrotononitrile by dimerization of acetonitrile. The process includes the reaction steps of deprotonating of the acetonitrile in the presence of a strong base, effecting salt formation of the 3-aminocrotononitrile and hydrolyzing the salt. The deprotonation with sodium amide as the strong base takes place in the presence of liquid ammonia.

The dimerization of acetonitrile, according to the process of the invention, takes place according to the mechanism:

(a) deprotonation of the acetonitrile in the presence of a strong base according to the formula:

(b) formation of the sodium salt of 3-aminocrotononitrile, by reaction of the acetonitrile carbanion with acetonitrile according to the formula:

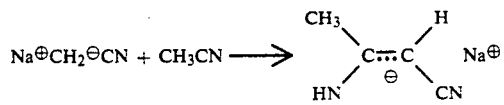

(c) and hydrolysis of the sodium salt of 3-aminocrotononitrile with water according to the formula:

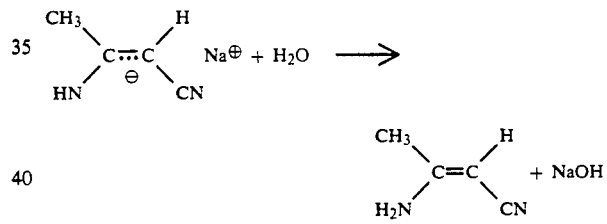

According to the invention, the deprotonation of the acetonitrile with the sodium amide are the strong base, which is produced in situ suitably ahead of time and in a known way [*F. W. Berostroem and W. C. Frenelius,* Chem. Rev., 12, (1933), 45 ff.] by the catalytic reaction of sodium with liquid ammonia, is performed in the presence of liquid ammonia. The deprotonation suitably takes place in the temperature range at which the ammonia is present at standard pressure in the liquid aggregation state, i.e., between −32° and −75° C. The deprotonation preferably takes place at a temperature between −32° to −35° C. The ammonia that is being freed in the deprotonation and the excess ammonia used as the solvent are suitably recycled and used for the production of the sodium amide.

It is advantageous to proceed so that the acetonitrile is added to the sodium amide produced in situ, which is present in an excess of liquid ammonia.

In this case, it is suitable to maintain a molar ratio of acetonitrile to sodium amide of 2 to 1.

The acetonitrile already in the inert solvent necessary for the subsequent salt formation, preferably in toluene, is suitably added to the sodium amide solution.

Instead of toluene, other aromatic hydrocarbons, such as, xylene or benzene, ethers, such as, tetrahydrofuran or dimethoxyethane, or amines, such as, aliphatic di- or trialkylamines, can be used as the inert solvent.

The deprotonation takes place quickly, so suitably directly after the addition it can be heated to the temperature, necessary for the formation of the sodium salt of the 3-aminocrotononitrile, of −5° to +35° C., preferably to room temperature.

In this case, the volatizing ammonia is collected and recycled.

Usually after about 0.5 to 2 hours, the salt formation is completed. Then, the sodium salt of the 3-aminocrotononitrile can be hydrolyzed by slow feeding of water to the reaction mixture in a known way, e.g., according to Swiss Patent No. 415,603, and converted in the 3-aminocrotononitrile.

Then the 3-aminocrotononitrile can be obtained from the reaction mixture in yields of over 90 percent and purities of over 99.5 percent in a manner known to one skilled in the art, preferably by distillation.

DETAILED DESCRIPTION OF THE INVENTION

Example 1

In a double-jacketed stirrer flushed with dry nitrogen, the sodium amide was produced with 250 ml of liquid ammonia under catalysis of 0.2 g of iron(III) nitrate from 13.8 g of sodium (0.6 mol). Within 25 minutes, a solution of 49.3 g of acetonitrile (1.2 mol) in 200 ml of toluene was instilled at the temperature of the liquid ammonia (−33°). After completion of the addition, the ammonia was evaporated. After the suspension had reached a temperature of 20° C. by heating, it was allowed to react for another hour at this temperature and the reaction mixture was then subjected to a slow hydrolysis by instilling 75 ml of water. After a reaction of 15 more minutes with stirring, the mixture was transferred for the phase separation into a separating funnel, and three phases were formed. After separation of the lower aqueous phase, which was extracted for purification another two times with 25 ml of solvent each, combined organic phases were first freed from toluene on the rotary evaporator in a water jet vacuum and then subjected to vacuum distillation. 99.7 to 99.8 percent 3-aminocrotononitrile was distilled over in a vacuum of 20 mbars and at a temperature of 134° to 140° C. The yield was 46.4 g (94.1 percent). The solvent toluene and the ammonia were recycled again into the process.

Examples 2 to 7

In these examples, other inert solvents instead of toluene were used, but the amount of the other feedstocks was kept constant.

| Ex. | Inert Solvent | Yield % | Purity % |
|---|---|---|---|
| 2 | xylene, 225 ml (isomer mixture) | 87.0 | 99.6 |
| 3 | benzene, 225 ml | 85.8 | 99.7 |
| 4 | dimethoxyethane (1, 2), 200 ml | 78.3 | 99.6 |
| 5 | tetrahydrofuran, 200 ml | 87.6 | 99.5 |
| 6 | diethylamine, 225 ml | 88.2 | 99.5 |
| 7 | triethylamine, 225 ml | 88.2 | 99.4 |

In all further aspects, the embodiments of Example 2 to 7 corresponds to Example 1.

COMPARISON EXAMPLE 1

In a thermostatically controllable double-jacketed stirrer, 24.3 g of diisopropylamine was dissolved in 100 ml of absolute tetrahydrofuran and 150 ml of a 0.16 molar solution of n-butyllithium in hexane was instilled with stirring at a temperature of a maximum of 20° C. After completion of the reaction, the reaction mixture was added to a solution of 19.7 g (0.48 mol) of acetonitrile in 60 ml of tetrahydrofuran at a maximum of −20° C. After completion of the addition, it was allowed to react for 30 more minutes at this temperature with stirring and was heated within 1 hour to 20° C., and a white mass was precipitated onto the vessel walls. After standing overnight, the reaction mixture was hydrolyzed at a temperature of 5° to 7° C. with a solution of 14.5 g of acetic acid in 50 ml of water. After the phase separation, the aqueous phase was extracted two more times with 25 ml of ether each time. The combined organic phases were freed of the solvent and of amine in a water jet vacuum by distillation. Distillation under the same conditions as in Example 1 produced 17.0 g of 3-aminocrotononitrile (86.3 percent yield) with a purity of 98.9 percent.

COMPARISON EXAMPLES 2 TO 4

As was shown in Examples 2 to 4, it was possible to expand the process to other secondary and silylated amines, which were used as auxiliary base in lithiated form. As a metallization reagent, a solution of n-butyllithium (0.16 mol in hexane) equivalent to the amount of amine was used.

| Comp. Ex. | Secondary Amine | Amount of Solvent (ml) | Reaction** Temperature (°C.) | Yield/Purity (%) |
|---|---|---|---|---|
| 2 | N-methylaniline 0.24 mol | tetrahydrofuran (160 ml) | −24° | 60/92.6 (crude product) |
| 3 | diethylamine 0.3 mol | diethyl ether (160 ml) | −23° | 56.9/99.0 |
| 4 | H—N(SiMe$_3$)$_2$ 0.6 mol | tetrahydrofuran 75 ml | 0° | 90.5/99.6 |

Note: ** temperature of the deprotonation

COMPARISON EXAMPLE 5

3.0 g (0.13 mol) of sodium metal in 115.5 g of hexamethyldisilazane (excess) was emulsified by a dispersing stirrer at a temperature of 124° C. Under the catalysis of 0.5 g of iron(III) stearate, the sodium salt was formed from hexamethyldisilazane within 5 hours and 30 minutes. Acetonitrile (10.7 g = 0.26 mol) was instilled at a temperature of 80° to 92° C. and the reaction mixture, cooled to 20° C., was filtered. The filter cake was washed with 30 ml of tert-butyl methyl ether and mixed u in 100 ml of water. After phase separation, the aqueous phase was extracted twice with 50 ml of ether and once with 25 ml of ether. The solvent was removed on the rotary evaporator and the residue was distilled under vacuum, and 5.7 g of 99.5 percent 3-aminocrotononitrile in a yield of 53.3 percent was obtained. From the filtrates, hexamethyldisilazane in a yield of up to 95 percent was recycled by fractionated distillation.

What is claimed is:

1. Process for the production of 3-aminocrotononitrile by dimerization of acetonitrile comprising the reaction steps of: deprotonating the acetonitrile in the presence of sodium amide in the presence of liquid ammonia at a temperature of between $-32°$ and $-77°$ C.; effecting salt formation of the 3-aminocrotononitrile at a temperature between $-5°$ and $+35°$ C. in the presence of an inert solvent; and hydrolyzing the salt to produce the 3-aminocrotononitrile.

2. Process according to claim 1 wherein the deprotonation takes place at standard pressure and at a temperature of the liquid ammonia between $-32°$ and $-35°$ C.

3. Process according to claim 2 wherein, for the dimerization, an excess of liquid ammonia, in relation to the acetonitrile, is used.

4. Process according to claim 3 wherein, for the dimerization, a molar ratio of acetonitrile to sodium amide of 2 to 1 is maintained.

5. Process according to claim 2 wherein the inert solvent is an aromatic hydrocarbon, an ether or an amine in the salt formation step.

6. Process according to claim 2 wherein toluene is used as the inert solvent in the salt formation step.

7. Process according to claim 6 wherein the hydrolysis is conducted by adding water.

8. Process according to claim 7 wherein the sodium amide is produced, before the dimerization, in situ by catalytic reaction of sodium with liquid ammonia.

9. Process according to claim 8 wherein the reaction steps comprising the dimerization are performed without isolating between the intermediate stages.

10. Process according to claim 1 wherein, for the dimerization, an excess of liquid ammonia, in relation to the acetonitrile, is used.

11. Process according to claim 1 wherein, for the dimerization, a molar ratio of acetonitrile to sodium amide of 2 to 1 is maintained.

12. Process according to claim 1 wherein the inert solvent is an aromatic hydrocarbon, an ether or an amine in the salt formation step.

13. Process according to claim 1 wherein toluene is used as the inert solvent int he salt formation step.

14. Process according to claim 1 wherein the hydrolysis is conducted by adding water.

15. Process according to claim 1 wherein the sodium amide is produced, before the dimerization, in situ by catalytic reaction of sodium with liquid ammonia.

16. Process according to claim 1 wherein the reaction steps comprising the dimerization are performed without isolating between the intermediate stages.

* * * * *